(12) United States Patent
Zhang

(10) Patent No.: US 11,932,684 B2
(45) Date of Patent: *Mar. 19, 2024

(54) ONLINE CHROMATOGRAPHY AND ELECTROSPRAY IONIZATION MASS SPECTROMETER

(71) Applicant: Regeneron Pharmaceuticals, Inc., Tarrytown, NY (US)

(72) Inventor: Qian Zhang, Lexington, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/117,634

(22) Filed: Mar. 6, 2023

(65) Prior Publication Data
US 2023/0204546 A1 Jun. 29, 2023

Related U.S. Application Data

(63) Continuation of application No. 16/750,287, filed on Jan. 23, 2020, now Pat. No. 11,630,092.
(Continued)

(51) Int. Cl.
*C07K 16/16* (2006.01)
*A61K 47/68* (2017.01)
(Continued)

(52) U.S. Cl.
CPC .......... *C07K 16/16* (2013.01); *A61K 47/6803* (2017.08); *G01N 30/7266* (2013.01);
(Continued)

(58) Field of Classification Search
CPC ................ C07K 16/16; C07K 2317/41; C07K 2317/522; C07K 2317/55; A61K 47/6803;
(Continued)

(56) References Cited

U.S. PATENT DOCUMENTS 6,737,634 B2 * 5/2004 Curtis ................... F04B 19/006
250/222.2
9,222,190 B2 * 12/2015 Nam ................... C23C 14/5853
(Continued)

FOREIGN PATENT DOCUMENTS

CN 101796408 A 8/2010
CN 105758953 A 7/2016
(Continued)

OTHER PUBLICATIONS

Shen M L et al: "Effect of enzyme inhibitors on protein quaternary structure determined by on-line size exclusion chromatography-microelectrospray ionization mass spectrometry," Journal of the American Society for Mass Spectrometry, Elsevier Science Inc, US, vol. 12, No. 1, Jan. 1, 2001 (Jan. 1, 2001), pp. 97-104.
(Continued)

*Primary Examiner* — David A Vanore
(74) *Attorney, Agent, or Firm* — Kramer Levin Naftalis & Frankel LLP

(57) ABSTRACT

Methods and system for protein characterization using online chromatography and electrospray ionization mass spectrometry are provided.

20 Claims, 12 Drawing Sheets

Related U.S. Application Data

(60) Provisional application No. 62/796,771, filed on Jan. 25, 2019.

(51) Int. Cl.
*G01N 30/72* (2006.01)
*G01N 30/80* (2006.01)
*G01N 33/68* (2006.01)
*H01J 49/16* (2006.01)

(52) U.S. Cl.
CPC ......... *G01N 30/80* (2013.01); *G01N 33/6848* (2013.01); *H01J 49/165* (2013.01)

(58) Field of Classification Search
CPC .............. G01N 30/7266; G01N 30/80; G01N 33/6848; G01N 30/38; G01N 30/48; G01N 30/74; H01J 49/165; B01D 15/34
See application file for complete search history.

(56) References Cited

U.S. PATENT DOCUMENTS

| | | | |
|---|---|---|---|
| 10,500,796 B1* | 12/2019 | Lazarovits | B29C 64/129 |
| 10,508,981 B2* | 12/2019 | Ndukaife | G21K 1/006 |
| 11,215,563 B2* | 1/2022 | Su | G02B 6/1226 |
| 11,630,092 B2* | 4/2023 | Zhang | G01N 30/7266 73/61.53 |
| 2014/0193325 A1* | 7/2014 | Nam | C01G 3/02 423/592.1 |
| 2019/0272894 A1 | 9/2019 | Wasalathanthri et al. | |
| 2020/0055043 A1* | 2/2020 | Medoro | B01L 3/502707 |
| 2020/0132697 A1 | 4/2020 | Yan et al. | |
| 2020/0230602 A1* | 7/2020 | Yao | G01N 15/1475 |
| 2020/0240965 A1 | 7/2020 | Zhang | |
| 2020/0240998 A1 | 7/2020 | Yan et al. | |
| 2020/0240999 A1 | 7/2020 | Wang | |

FOREIGN PATENT DOCUMENTS

| | | |
|---|---|---|
| CN | 108027371 A | 5/2018 |
| WO | WO2019152303 A1 | 8/2019 |

OTHER PUBLICATIONS

Markus Haberger et al: "Rapid characterization of biotherapeutic proteins by size-exclusion chromatography coupled to native mass spectrometry," MABS, vol. 8, No. 2,Dec. 10, 2015 (Dec. 10, 2015), pp. 331-339.
Alexandru C. Lazar et al: "Analysis of the composition of immunoconjugates using size-exclusion chromatography coupled to mass spectrometry," Rapid Communications in Mass Spectrometry, vol. 19, No. 13,Jan. 1, 2005 (Jan. 1, 2005), pp. 1806-1814.
B Kukrer et al: "Mass Spectrometric, Analysis of Intact Human Monoclonal Antibody Aggregates Fractionated by Size-Exclusion Chromatography," Pharmaceutical Research, Kluwer Academic Publishers-Plenum Publishers, NL, vol. 27, No. 10, Aug. 3, 2010 (Aug. 3, 2010), pp. 2197-2204.
International Search Report Application No. PCT/US2020/014721, Filing Date Jan. 23, 2020, dated May 11, 2020.
Cavanagh J. et al. In-line desalting mass spectrometry for the study of non-covalent biological complexes. Analytical chemistry, 2003, V. 75, No. 14, p. 3281-3286.
Cavanagh J. et al. Stoichiometries of Protein-Protein/DNA Binding and Conformational Changes for the Transition-State Regulator AbrB Measured by Pseudo Cell-Size Exclusion Chromatography-Mass Spectrometry. Biochemistry, 2002, V. 41, No. 25, p. 7859-7865.

* cited by examiner

ONLINE CHROMATOGRAPHY AND ELECTROSPRAY IONIZATION MASS SPECTROMETER

CROSS-REFERENCE TO RELATED APPLICATIONS

This application is a continuation of U.S. patent application Ser. No. 16/750,287, filed Jan. 23, 2020, which claims priority to and the benefit of U.S. Provisional Patent Application No. 62/796,771 filed Jan. 25, 2019, the content of which is hereby incorporated by reference in its entirety.

FIELD

The invention generally pertains to a method for characterizing protein biopharmaceuticals using online chromatography and electrospray ionization mass spectrometry.

BACKGROUND

Protein biopharmaceutical products have emerged as important drugs for the treatment of cancer, autoimmune disease, infection and cardiometabolic disorders, and they represent one of the fastest growing product segments of the pharmaceutical industry.

Protein biopharmaceutical products must meet very high standards of purity. Thus, it can be important to monitor and characterize protein biopharmaceuticals during different stages of drug development and production. Analytical method for assays for characterization of such protein biopharmaceuticals should display sufficient accuracy and resolution to detect and quantify the desired product. Evaluation can be difficult due to similarities between structural and physicochemical properties of the protein biopharmaceutical compared to its mutated or modified or cleaved form. Direct analysis can require isolation of the product in a sufficiently large amount for assay, which is undesirable and has only been possible in selected cases.

There is a long felt need in the art for a method and/or system for characterizing protein biopharmaceuticals.

SUMMARY

Growth in the development, manufacture and sale of protein biopharmaceutical products has led to an increasing demand for characterizing the protein biopharmaceutical along with possible impurities, binding stoichiometry and its overall composition.

Exemplary embodiments disclosed herein satisfy the aforementioned demands by providing methods for characterizing, identifying and/or quantifying a protein biopharmaceutical along with its possible impurities, binding and overall composition.

This disclosure, at least in part, provides a method for characterization of a protein. In one exemplary embodiment, the method for characterization of a protein comprises contacting a sample including the protein to a chromatographic system with a chromatography resin, washing said resin using a mobile phase to provide an eluent including the protein, and characterizing the protein in said eluent using an electrospray ionization mass spectrometer.

In one aspect of this embodiment, the method for characterization of a protein can comprise a chromatographic system with a size exclusion chromatography resin In one aspect of this embodiment, the method for characterization of a protein can comprise coupling an electrospray ionization mass spectrometer to a chromatographic system with a chromatography resin.

In one aspect of this embodiment, the method for characterization of a protein can comprise coupling an electrospray ionization mass spectrometer to a chromatographic system having a size-exclusion chromatography resin.

In one aspect, the method for characterization of a protein can comprise an electrospray ionization mass spectrometer operating under native conditions.

In one aspect of this embodiment, the method for characterization of a protein can comprise a nano-electrospray ionization mass spectrometer.

In one aspect of this embodiment, the method for characterization of a protein can comprise a nano-electrospray ionization mass spectrometer operating under native conditions.

In one aspect of this embodiment, the method for characterization of a protein can comprise at least one three way-splitter to couple an electrospray ionization mass spectrometer to a chromatographic system with a resin.

In one aspect of this embodiment, the method for characterization of a protein can comprise at least one three way-splitter to couple an ultraviolet detector to the chromatographic system with a resin.

In one aspect of this embodiment, the method for characterization of a protein can comprise at least one three way-splitter to couple an ultraviolet detector and electrospray ionization mass spectrometer to a chromatographic system with a resin.

In one aspect of this embodiment, the method for characterization of a protein can comprise at least one three way-splitter to couple an electrospray ionization mass spectrometer to a chromatographic system with a size exclusion chromatography resin.

In one aspect of this embodiment, the method for characterization of a protein can comprise at least one three way-splitter to couple an ultraviolet detector to the chromatographic system with a size exclusion chromatography resin.

In one aspect of this embodiment, the method for characterization of a protein can comprise at least one three way-splitter to couple an ultraviolet detector and electrospray ionization mass spectrometer to a chromatographic system with a size exclusion chromatography resin.

In one aspect of this embodiment, the method for characterization of a protein can comprise washing a resin using the mobile phase to provide an eluent including the protein, wherein the eluent is introduced in an ultraviolet detector through at least one three way-splitter at a flow rate of about 0.2 mL/min to about 0.4 mL/min.

In one aspect of this embodiment, the method for characterization of a protein can comprise a mobile phase comprising a volatile salt.

In one aspect of this embodiment, the method for characterization of a protein can comprise a mobile phase comprising ammonium acetate.

In one aspect of this embodiment, the method for characterization of a protein can comprise a mobile phase with a total concentration of less than about 100 mM of Ammonium Acetate.

In one aspect of this embodiment, the method for characterization of a protein can comprise washing a resin with the mobile phase with a flow rate of about 0.2 mL/min to about 0.4 mL/min.

In one aspect of this embodiment, the method for characterization of a protein can comprise a mobile phase with a pH of about 6.8.

In one aspect of this embodiment, the method for characterization of a protein can comprise a sample including the protein in an amount of about 10 µg to about 100 µg of the protein.

In one aspect of this embodiment, the method for characterization of a protein can comprise a protein that is an antibody.

In one aspect of this embodiment, the method for characterization of a protein can comprise a protein that is an antigen-antibody complex.

In one aspect of this embodiment, the method for characterization of a protein can comprise a protein that is an antibody-drug conjugate.

In one aspect of this embodiment, the method for characterization of a protein can comprise an electrospray ionization mass spectrometer with a flow rate of about 10 nL/min to about 50 nL/min.

In one aspect of this embodiment, the method for characterization of a protein can comprise an electrospray ionization mass spectrometer with a spray voltage of an electrospray is about 0.8 kV to about 1.5 kV.

In one aspect of this embodiment, the method for characterization can comprise identifying the protein.

In one aspect of this embodiment, the method for characterization of a protein can comprise quantifying the protein.

In one aspect of this embodiment, the method for characterization of a protein can comprise quantifying the relative abundance of the protein.

In one aspect of this embodiment, the method for characterization of a protein can comprise a sample with at least two proteins.

This disclosure, at least in part, provides a method for characterization of an antibody-drug conjugate. In one exemplary embodiment, the method for characterization of an antibody-drug conjugate comprises contacting a sample including the antibody-drug conjugate to a chromatographic system with a chromatography resin, washing said resin using a mobile phase to provide an eluent including the antibody-drug conjugate, and characterizing the antibody-drug conjugate in said eluent using an electrospray ionization mass spectrometer.

In one aspect of this embodiment, the method for characterization of an antibody-drug conjugate can comprise a chromatographic system with a size exclusion chromatography resin In one aspect of this embodiment, the method for characterization of an antibody-drug conjugate can comprise coupling an electrospray ionization mass spectrometer to a chromatographic system with a chromatography resin.

In one aspect of this embodiment, the method for characterization of an antibody-drug conjugate can comprise coupling an electrospray ionization mass spectrometer to a chromatographic system having a size-exclusion chromatography resin.

In one aspect of this embodiment, the method for characterization of an antibody-drug conjugate can comprise an electrospray ionization mass spectrometer under native conditions.

In one aspect of this embodiment, the method for characterization of an antibody-drug conjugate can comprise a nano-electrospray ionization mass spectrometer.

In one aspect of this embodiment, the method for characterization of an antibody-drug conjugate can comprise a nano-electrospray ionization mass spectrometer operating under native conditions.

In one aspect of this embodiment, the method for characterization of an antibody-drug conjugate can comprise at least one three way-splitter to couple an electrospray ionization mass spectrometer to a chromatographic system with a resin.

In one aspect of this embodiment, the method for characterization of an antibody-drug conjugate can comprise at least one three way-splitter to couple an ultraviolet detector to the chromatographic system with a resin.

In one aspect of this embodiment, the method for characterization of an antibody-drug conjugate can comprise at least one three way-splitter to couple an ultraviolet detector and electrospray ionization mass spectrometer to a chromatographic system with a resin.

In one aspect of this embodiment, the method for characterization of an antibody-drug conjugate can comprise at least one three way-splitter to couple an electrospray ionization mass spectrometer to a chromatographic system with a size exclusion chromatography resin.

In one aspect of this embodiment, the method for characterization of an antibody-drug conjugate can comprise at least one three way-splitter to couple an ultraviolet detector to the chromatographic system with a size exclusion chromatography resin.

In one aspect of this embodiment, the method for characterization of an antibody-drug conjugate can comprise at least one three way-splitter to couple an ultraviolet detector and electrospray ionization mass spectrometer to a chromatographic system with a size exclusion chromatography resin.

In one aspect of this embodiment, the method for characterization of an antibody-drug conjugate can comprise washing a resin using the mobile phase to provide an eluent including the an antibody-drug conjugate, wherein the eluent is introduced in an ultraviolet detector through at least one three way-splitter at a flow rate of about 0.2 mL/min to about 0.4 mL/min.

In one aspect of this embodiment, the method for characterization of an antibody-drug conjugate can comprise a mobile phase comprising a volatile salt.

In one aspect of this embodiment, the method for characterization of an antibody-drug conjugate can comprise a mobile phase comprising ammonium acetate.

In one aspect of this embodiment, the method for characterization of an antibody-drug conjugate can comprise a mobile phase with a total concentration of less than about 100 mM of ammonium acetate.

In one aspect of this embodiment, the method for characterization of an antibody-drug conjugate can comprise washing a resin with the mobile phase with a flow rate of about 0.2 mL/min to about 0.4 mL/min.

In one aspect of this embodiment, the method for characterization of an antibody-drug conjugate can comprise a mobile phase with a pH of about 6.8.

In one aspect of this embodiment, the method for characterization of an antibody-drug conjugate can comprise a sample including the protein in an amount of about 10 µg to about 100 µg of the antibody-drug conjugate.

In one aspect of this embodiment, the method for characterization of an antibody-drug conjugate can comprise washing the resin using a mobile phase to provide an eluent which is introduced in the electrospray ionization mass spectrometer at a flow rate of less than about 50 µl/min.

In one aspect of this embodiment, the method for characterization of an antibody-drug conjugate can comprise an electrospray ionization mass spectrometer with a flow rate of about 10 nL/min to about 50 nL/min.

In one aspect of this embodiment, the method for characterization of an antibody-drug conjugate can comprise an electrospray ionization mass spectrometer with a spray voltage of an electrospray is about 0.8 kV to about 1.5 kV.

In one aspect of this embodiment, the method for characterization of an antibody-drug conjugate can comprise an antibody-drug conjugate that is an site-specific antibody-drug conjugate.

In one aspect of this embodiment, the method for characterization of an antibody-drug conjugate can comprise an antibody-drug conjugate that is a not a site-specific antibody-drug conjugate.

In one aspect of this embodiment, the method for characterization of an antibody-drug conjugate can comprise an antibody-drug conjugate that is an engineered cysteine-based antibody-drug conjugate.

In one aspect of this embodiment, the method for characterization of an antibody-drug conjugate can comprise an antibody-drug conjugate that is a non-specific cysteine-based antibody-drug conjugate.

In one aspect of this embodiment, the method for characterization of an antibody-drug conjugate can comprise characterizing drug-to-antibody ratio.

In one aspect of this embodiment, the method for characterization of an antibody-drug conjugate can comprise identifying the antibody.

In one aspect of this embodiment, the method for characterization of an antibody-drug conjugate can comprise quantifying the antibody.

This disclosure, at least in part, provides a system comprising a chromatographic column having a chromatography resin. In another exemplary embodiment, the system comprise a chromatographic column having a chromatography resin, wherein the chromatographic column is capable of receiving a mobile phase and a sample including a protein, and an electrospray ionization mass spectrometer.

In one aspect of this embodiment, the system can comprise a chromatographic column having a size exclusion chromatography resin.

In one aspect of this embodiment, the system can comprise an electrospray ionization mass spectrometer capable of being coupled to said chromatographic column.

In one aspect of this embodiment, the system can comprise an electrospray ionization mass spectrometer capable of being run under native conditions.

In one aspect of this embodiment, the system can comprise a nano electrospray ionization mass spectrometer.

In one aspect of this embodiment, the system can comprise a chromatographic column capable of being coupled to a mass spectrometer using a three way splitter.

In one aspect of this embodiment, the system can comprise a chromatographic column capable of being coupled to an ultraviolet detector using a three way splitter.

In one aspect of this embodiment, the system can comprise a chromatographic column capable of being coupled to an ultraviolet detector and a mass spectrometer using a three way splitter.

In one aspect of this embodiment, the system can be capable of characterizing drug to antibody ratio of an antibody-drug conjugate.

In one aspect of this embodiment, the system can be capable of characterizing a protein.

In one aspect of this embodiment, the system can be capable of characterizing an antigen-antibody complex.

DETAILED DESCRIPTION

Figure 1:
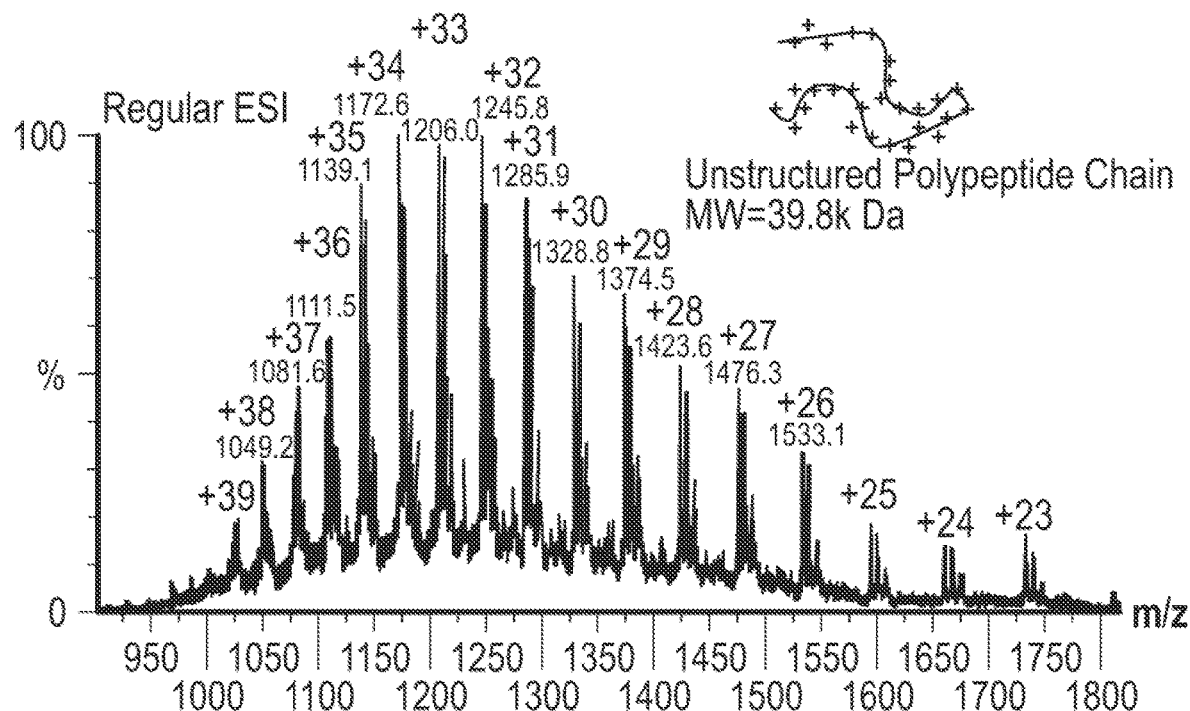
FIG. 1 shows spectra obtained from regular and native electrospray ionization mass spectrometry.
Figure 1:
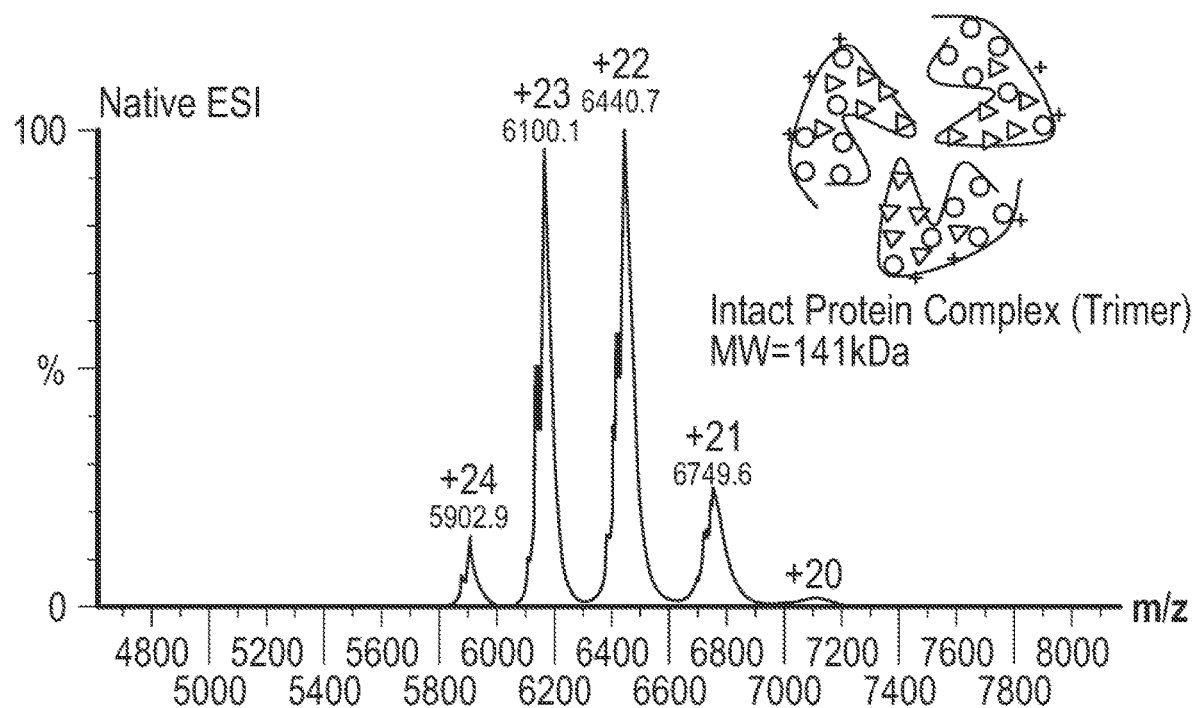

Identification and quantification of proteins in protein biopharmaceutical products can be very important during the production and development of a product. The presence of impurities and the method of binding of a protein biopharmaceutical product can be imperative into developing a safe and effective product. Hence, a robust method and/or workflow to characterize the protein biopharmaceutical, its method of binding, and characterizing any accompanying impurities can be beneficial.

One of the methods includes use of size exclusion chromatography (SEC) for characterizing biomolecular aggregation and fragmentation in the biotech industry (Hong Paule et al., *Size-Exclusion Chromatography for the Analysis of Protein Biotherapeutics and their Aggregates*, 35 JOURNAL OF LIQUID CHROMATOGRAPHY AND RELATED TECHNOLOGY 2923-2950 (2012)). The separation of molecules by SEC relies on the differential interaction of molecules with a controlled porous structure on a stationary phase. As SEC uses buffer conditions that preserve the native structure of proteins in solution, it permits characterization of biomolecules without disturbing their native conformation. Among the various detection modes that can be coupled with SEC, mass spectrometry (MS) allows for the precise and accurate identification of individual components in complex samples. The combination of SEC and MS has been reported previously, including the collection of SEC peaks followed by direct infusion MS (Başak Kükrer et al., *Mass Spectrometric Analysis of Intact Human Monoclonal Antibody Aggregates Fractionated by Size-Exclusion Chromatography*, 27 PHARMACEUTICAL RESEARCH 2197-2204 (2010); François Debaene et al., *Innovative Native MS Methodologies for Antibody Drug Conjugate Characterization: High Resolution Native MS and IM-MS for Average DAR and DAR Distribution Assessment*, 86 ANALYTICAL CHEMISTRY 10674-10683 (2014)) or online SEC-MS (Khaja Muneeruddin et al., *Characterization of Small Protein Aggregates and Oligomers Using Size Exclusion Chromatography with Online Detection by Native Electrospray Ionization Mass Spectrometry*, 86 ANALYTICAL CHEMISTRY 10692-10699 (2014); C. F. Mcdonagh et al., *Engineered antibody-drug conjugates with defined sites and stoichiometries of drug attachment*, 19 PROTEIN ENGINEERING DESIGN AND SELECTION 299-307 (2006)). However, to directly ionize the high flow generated from SEC separation requires harsh ionization conditions that are often incompatible with native MS analysis, thereby limiting the utility of coupling these technologies for the analysis of non-covalent interactions. Further, the sensitivity of the mass spectrometer can suffer from the high salt concentrations used in SEC buffers.

As non-covalent protein interactions mediate such a broad spectrum of biological functions, there is a growing interest in developing methods that facilitate the study of their structure, stoichiometry and dynamics. Such methods can aid to investigate the non-covalent protein interactions that occur widely in nature and coordinate the interaction of protein biopharmaceuticals with a diversity of molecules, including other proteins and peptides, nucleic acids, lipids, and inorganic and organic small molecules are also required. Size-exclusion chromatography (SEC) allows for the isolation of biomolecules from heterogeneous mixtures of molecular components and, because the buffer conditions maintain proteins in their native conformation, SEC is an ideal method for preserving non-covalent biomolecular complexes during their isolation. Among the various detection methods that can be coupled with SEC analysis, mass spectrometry (MS) allows for the confident identification and characterization of individual components from complex mixtures. However, the high-flow rate and non-volatile salts used in SEC often are not compatible with downstream MS analysis.

Considering the limitations of existing methods, an effective and efficient method for analysis of protein biopharmaceuticals using online chromatography with electrospray ionization MS platform was developed.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure provides a method for characterizing, identifying and/or quantifying a protein biopharmaceutical.

As used herein, a "protein biopharmaceutical" includes an active ingredient which is fully or partially biological in nature. In some exemplary embodiments, the protein biopharmaceutical can comprise a protein, vaccine, allergen, nucleic acids, virus, antibody-drug conjugate, cells, gene, tissues, or combinations thereof. In some other exemplary embodiments, the protein biopharmaceutical can comprise a recombinant, engineered, modified, mutated, or truncated version of a protein, vaccine, allergen, nucleic acids, virus, antibody-drug conjugate, cells, gene, tissues, or combinations thereof.

As used herein, the term "protein" includes any amino acid polymer having covalently linked amide bonds. Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect baculovirus system, yeast systems (e.g., *Pichia* sp.), mammalian systems (e.g., CHO cells and CHO derivatives like CHO-K1 cells). For a review discussing biotherapeutic proteins and their production, see Ghaderi et al., "Production platforms for biotherapeutic glycoproteins. Occurrence, impact, and challenges of non-human sialylation," (BIOTECHNOL. GENET. ENG. REV. 147-175 (2012)). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins.

In some exemplary embodiments, the protein can be an antibody, a bispecific antibody, a multispecific antibody, antibody fragment, monoclonal antibody, host-cell protein or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_{H2}$ and $C_H3$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

As used herein, the term "antibody-drug conjugate" or "ADC" can refer to antibody attached to biologically active drug(s) by linker(s) with labile bond(s). An ADC can comprise several molecules of a biologically active drug (or the payload) which can be covalently linked to side chains of amino acid residues of an antibody (Siler Panowski et al., *Site-specific antibody drug conjugates for cancer therapy*, 6 MABS 34-45 (2013)). An antibody used for an ADC can be capable of binding with sufficient affinity for selective accumulation and durable retention at a target site. Most ADCs can have Kd values in the nanomolar range. The payload can have potency in the nanomolar/picomolar range and can be capable of reaching intracellular concentrations achievable following distribution of the ADC into target tissue. Finally, the linker that forms the connection between the payload and the antibody can be capable of being sufficiently stable in circulation to take advantage of the pharmacokinetic properties of the antibody moiety (i.e., long half-life) and to allow the payload to remain attached to the antibody as it distributes into tissues, yet should allow for efficient release of the biologically active drug d once the ADC is taken up into target cells.

The linker can be: those that are non-cleavable during cellular processing and those that are cleavable once the ADC has reached the target site. With non-cleavable linkers, the biologically active drug released within the call includes the payload and all elements of the linker still attached to an amino acid residue of the antibody, typically a lysine or cysteine residue, following complete proteolytic degradation of the ADC within the lysosome. Cleavable linkers are those whose structure includes a site of cleavage between the payload and the amino acid attachment site on the antibody. Cleavage mechanisms can include hydrolysis of acid-labile bonds in acidic intracellular compartments, enzymatic cleavage of amide or ester bonds by an intracellular protease or esterase, and reductive cleavage of disulfide bonds by the reducing environment inside cells.

In some specific embodiments, the disclosure also provides a method for identifying the drug-to-antibody ratio (DAR) for an antibody-drug conjugate.

ADCs can be made by conjugation to endogenous amino acid residues of the antibody, carefully controlling the average degree of modification to yield an optimum drug-to-antibody ratio (DAR). This ratio can be selected on the basis of (a) minimizing the amount of non-conjugated antibody and (b) avoiding species in the mixture with very high DAR, which may be problematic in manufacturing and formulation because of higher hydrophobicity and lower solubility, and may result in poor pharmacokinetic properties. Attaching too few of the biologically active drug molecules will lead to decreased efficacy, whereas too many can make the ADC unstable with altered pharmacokinetic properties, increased plasma clearance, reduced half-life and increased systemic toxicity. An optimal DAR is often undetermined and highly dependent on other ADC variables; however, more commonly the ADCs aim to attain a DAR close to 4. Non-limiting example of conjugation of the biologically active drug to an antibody can include conjugation of the biologically active drug to lysine or cysteine residues on the antibody. The lysine conjugation can result in 0-8 conjugated biologically active drug molecules per antibody and can occur on both the heavy and light chain at different lysine residues. Another non-limiting example of conjugation of the biologically active drug to an antibody can include cysteine conjugation which occurs after reduction of four inter-chain disulfide bonds, and the conjugation is thus limited to the eight exposed sulfhydryl groups and hence the linked biologically active drug molecules per antibody can range from 0-8. The diversity in heterogeneity of an ADC mixture is 2-fold because these ADC species differ in drug load and conjugation site. Therefore, each species may have distinct properties, which may result in a wide range of in vivo PK properties. In addition, batch-to-batch consistency in ADC production can be challenging and may require diligent manufacturing capabilities.

Site-specific antibody-drug conjugation, in which a known number of biologically active drug molecules are consistently conjugated to defined sites, is one way to overcome these challenges. Heterogeneity is minimized and ADC properties are more predictable, with consistent conjugate production from batch to batch. The drug-to-antibody ratio (DAR) is precisely controlled and can be tailored to various linked biologically active drugs, producing either 2- or 4-DAR site-specific ADCs. Non-limiting examples of site-specific conjugation include linking the biologically active drug molecule to the antibody through engineered cysteine residue, glutamine residue, unnatural amino acids (e.g., p-acetylphenylalanine, N6-((2-azidoethoxy)carbonyl)-L-lysine, p-azidomethyl-L-phenylalanine, selenocysteine), glycans, or short peptide tags as taught by Qun Zhou in the review "Site-Specific Antibody Conjugation for ADC and Beyond" which is incorporated by reference (Qun Zhou, *Site-Specific Antibody Conjugation for ADC and Beyond*, 5 BIOMEDICINES 64 (2017)).

In some exemplary embodiments, the disclosure provides a method for characterizing, identifying and/or quantifying at least one impurity in a protein biopharmaceutical product.

As used herein, the term "impurity" can include any undesirable protein present in the protein biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S—S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See European Bioinformatics InstituteProtein Information ResourceSIB Swiss Institute of Bioinformatics, EUROPEAN BIOINFORMATICS INSTITUTE DRS-DROSOMYCIN PRECURSOR-DROSOPHILA MELANOGASTER (FRIUT FLY)-DRS GENE & PROTEIN, http://www.uniprot.org/docs/ptmlist (last visited Jan. 15, 2019) for a more detailed controlled vocabulary of PTMs curated by UniProt.

As used herein, the term "desired product" refers to the protein biopharmaceutical which has the desired structure, function, or efficacy profile.

In some exemplary embodiments, the disclosure also provides a method for characterizing the binding of a protein biopharmaceutical. For example, antibodies can bind antigens through highly specific, high-affinity non-covalent interactions, a property that has enabled the development of therapeutic antibodies to target disease-specific antigens in the treatment of a variety of diseases (Andrew C. Chan & Paul J. Carter, *Therapeutic antibodies for autoimmunity and inflammation*, 10 NATURE REVIEWS IMMUNOLOGY 301-316 (2010)). In order to develop effective antibody therapeutics, it can be crucial to understand how antibody binding affects the function of the targeted protein.

In some exemplary embodiments, the disclosure also provides a method for identifying the binding ratio of antibody to antigen from an antigen-antibody complex.

In some specific exemplary embodiments, the disclosure also provides a method for identifying the antigen to which an antibody binds. In some other exemplary embodiments, the method can comprise determining whether a cleaved, modified, or mutated version(s) of an antigen and/or antibody are responsible for an antigen-antibody complex.

In some exemplary embodiments, the disclosure also provides a method for quantifying the relative abundance of individual proteins in solution.

In some exemplary embodiments, the method for characterizing, identifying and/or quantifying a protein biopharmaceutical, its possible impurities, binding or composition can comprise contacting a sample including the protein biopharmaceutical to a chromatographic system having a chromatographic resin.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

As used herein, the term "Mixed Mode Chromatography (MMC)" or "multimodal chromatography" includes a chromatographic method in which solutes interact with stationary phase through more than one interaction mode or mechanism. MMC can be used as an alternative or complementary tool to traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings and operation flexibility compared to affinity based methods.

In some exemplary embodiments, the chromatography can be size-exclusion chromatography.

As used herein, the terms "SEC chromatography resin" or "SEC chromatography media" are used interchangeably and can include any kind of solid phase used in SEC which separates the impurity from the desired product (e.g., a homodimer contaminant for a bispecific antibody product). The volume of the resin, the length and diameter of the column to be used, as well as the dynamic capacity and flow-rate can depend on several parameters such as the volume of fluid to be treated, concentration of protein in the fluid to be subjected to the process.

In some exemplary embodiments, the method for characterizing, identifying and/or quantifying a protein biopharmaceutical, its possible impurities, binding or composition can comprise contacting a sample including the protein biopharmaceutical to a chromatographic system having a size-exclusion chromatography resin, washing said size-exclusion chromatography resin using a mobile phase to provide an eluent including the protein; and characterizing the protein in said eluent using an electrospray ionization mass spectrometer.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "electrospray infusion setup" refers to an electrospray ionization system that is compatible with a mass spectrometer used for mass analysis of protein. In electrospray ionization, an electrospray needle has its orifice positioned close to the entrance orifice of a spectrometer. A sample, containing the protein of interest, can be pumped through the syringe needle. An electric potential between the syringe needle orifice and an orifice leading to the mass analyzer forms a spray ("electrospray") of the solution. The electrospray can be carried out at atmospheric pressure and provides highly charged droplets of the solution. The electrospray infusion setup can include an electrospray emitter, nebulization gas, and/or an ESI power supply. The setup can optionally be automated to carry out sample aspiration, sample dispensing, sample delivery, and/or for spraying the sample.

In some exemplary embodiments, the electrospray ionization mass spectrometer can be a nano-electrospray ionization mass spectrometer.

The term "nanoelectrospray" or "nanospray" as used herein refers to electrospray ionization at a very low solvent flow rate, typically hundreds of nanoliters per minute of sample solution or lower, often without the use of an external solvent delivery. The electrospray infusion setup forming a nanoelectrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

As used herein, the term "mass analyzer" includes a device that can separate species, that is, atoms, molecules, or clusters, according to their mass. Non-limiting examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

In some exemplary embodiments, mass spectrometry can be performed under native conditions.

As used herein, the term "native conditions" or "native MS" or "native ESI-MS" can include a performing mass spectrometry under conditions that preserve no-covalent interactions in an analyte. For detailed review on native MS, refer to the review: Eisabetta Boeri Erba & Carlo Petosa, *The emerging role of native mass spectrometry in characterizing the structure and dynamics of macromolecular complexes*, 24 PROTEIN SCIENCE 1176-1192 (2015). Some of the distinctions between native ESI and regular ESI are illustrated in table 1 and FIG. 1 (Hao Zhang et al., *Native mass spectrometry of photosynthetic pigment-protein complexes*, 587 FEBS Letters 1012-1020(2013)).

TABLE 1

|  | Native ESI | Regular ESI |
| --- | --- | --- |
| Sample Solution | Aqueous solution water, ammonium acetate | Partial organic solution water, formic acid, acetonitrile/Methanol (pH 1-2) |
| Spray Condition | 10-50 nL/min Spray voltage 0.8~1.5 kV Temperatures 20-30° C. | 10-50 nL/min Spray voltage 0.8~1.5 kV Temperatures 20-30° C. |
| Salt Treatment | Offline Desalt | Online/Offline Desalt with RP-HPLC |
| Protein Concentration | 1-10 µM (complex) | <1 µM (subunit) |
| Output Information | Molecular weight of protein complex and subunit Non-covalent interactions Stoichiometry Structure | Molecular weight of a single subunit |

In some exemplary embodiments, the mass spectrometer can be a tandem mass spectrometer.

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information or the fragment ion signal is detectable. Tandem MS have been successfully performed with a wide variety of analyzer combinations. What analyzers to combine for a certain application is determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometer ions produced in the ion source can be trapped, isolated, fragmented, and m/z separated in the same physical device.

The peptides identified by the mass spectrometer can be used as surrogate representatives of the intact protein and their post-translational modifications. They can be used for protein characterization by correlating experimental and theoretical MS/MS data, the latter generated from possible peptides in a protein sequence database. The characterization can include, but is not limited, to sequencing amino acids of the protein fragments, determining protein sequencing, determining protein de novo sequencing, locating post-translational modifications, or identifying post translational modifications, or comparability analysis, or combinations thereof.

As used herein, the term "database" refers to bioinformatics tools which provide the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMSSA (http://www.pubchem.ncbi.nlm.nih.gov/omssa/), X!Tandem (http://www.thegpm.org/TANDEM/), Protein Prospector (http://www.http://prospector.ucsf.edu/prospector/mshome.htm), Byonic (https://www.proteinmetrics.com/products/byonic) or Sequest (http://fields.scripps.edu/sequest).

Exemplary Embodiments

Embodiments disclosed herein provide compositions, methods, and systems for the rapid characterization of proteins in a sample.

This disclosure provides a method for characterization of a protein, comprising contacting a sample including the protein to a chromatographic system with a chromatography resin, washing said resin using a mobile phase to provide an eluent including the protein, and characterizing the protein in said eluent using an electrospray ionization mass spectrometer.

This disclosure provides a method for characterization of an antibody-drug conjugate, comprising contacting a sample including the antibody-drug conjugate to a chromatographic system with a chromatography resin, washing said resin using a mobile phase to provide an eluent including the antibody-drug conjugate, and characterizing the antibody-drug conjugate in said eluent using an electrospray ionization mass spectrometer.

This disclosure provides a method for characterization of an antigen-antibody complex, comprising contacting a sample including the antigen-antibody complex to a chromatographic system with a chromatography resin, washing said resin using a mobile phase to provide an eluent including the antigen-antibody complex, and characterizing the antigen-antibody complex in said eluent using an electrospray ionization mass spectrometer.

In some exemplary embodiments, the chromatographic system can include traditional reversed-phased (RP), ion exchange (IEX) or normal phase chromatography (NP).

In some exemplary embodiments, the chromatographic resin can be selected from affinity chromatography resin, anion-exchange resin, cation exchange resin, affinity resin, mixed mode chromatography resin, hydrophobic interaction chromatography resin or size exclusion chromatography resin.

In some exemplary embodiments, the electrospray ionization mass spectrometer can be a nano-electrospray ionization mass spectrometer.

In some exemplary embodiments, the electrospray ionization mass spectrometer can be coupled to a chromatographic system with a chromatography resin.

In some exemplary embodiments, the electrospray ionization mass spectrometer can be run under native conditions.

In some exemplary embodiments, the chromatographic system can be coupled to the electrospray ionization mass spectrometer using a three-way splitter.

In some exemplary embodiments, the chromatographic system can be coupled to an ultraviolet detector using a three-way splitter.

In some exemplary embodiments, the chromatographic system can be coupled to the electrospray ionization mass spectrometer and an ultraviolet detector using a three-way splitter.

In some exemplary embodiments, the chromatographic system can be coupled to an electrospray ionization mass spectrometer and an ultraviolet detector using a three-way splitter, wherein the electrospray ionization mass spectrometer is a nano-electrospray ionization mass spectrometer.

In some exemplary embodiments, the chromatographic system can be coupled to an electrospray ionization a mass spectrometer and an ultraviolet detector using a three-way splitter, wherein the mass spectrometer is an electrospray ionization mass spectrometer operating under native conditions.

In some exemplary embodiments, the chromatographic system can be coupled to an electrospray ionization mass spectrometer and an ultraviolet detector using a three-way splitter, wherein the electrospray ionization mass spectrometer is a nano-electrospray ionization mass spectrometer under native conditions.

In some exemplary embodiments, the eluent including the protein or antigen-antibody complex or antibody-drug conjugate from washing the resin is introduced in an ultraviolet detector through at least one three way-splitter at a flow rate of about 0.2 mL/min to about 0.4 mL/min.

In some exemplary embodiments, the mobile phase for washing has a flow rate of about 0.2 mL/min to about 0.4 mL/min.

In some exemplary embodiments, the mobile phase can comprise a volatile salt. In some specific embodiments, the mobile phase can comprise ammonium acetate, ammonium bicarbonate, or ammonium formate, or combinations thereof.

In some exemplary embodiments, the mobile phase used can be compatible with the mass spectrometer.

In some exemplary embodiments, the mobile phase can have a pH of about 6.0-8.0.

In some exemplary embodiments, the sample can be used in amount of about 10 μg to about 100 μg of the protein or antigen-antibody complex or antibody-drug conjugate.

In some exemplary embodiments, the flow rate in the electrospray ionization mass spectrometer can be about 10 nL/min to about 50 nL/min.

In some exemplary embodiments, the electrospray ionization mass spectrometer can have a spray voltage of about 0.8 kV to about 1.5 kV.

In some exemplary embodiments, characterization can include identifying and/or quantifying the protein. In one aspect, characterization can include protein sequencing, protein de novo sequencing, identifying post-translational modifications, or comparability analysis, or combinations thereof. In another aspect, characterization can include quantifying the relative abundance of the protein.

In some exemplary embodiments, characterization can include identifying and/or quantifying the antibody in an antibody-drug conjugate. In one aspect, characterization can include protein sequencing, protein de novo sequencing, identifying post-translational modifications, or comparability analysis, or combinations thereof. In another aspect, characterization can include quantifying the relative abundance of the antibody in an antibody-drug conjugate.

In some exemplary embodiments, characterization can include identifying and/or quantifying the antibody and/or antigen in an antigen-antibody complex. In one aspect, characterization can include protein sequencing, protein de novo sequencing, identifying post-translational modifications, or comparability analysis, or combinations thereof for the antibody or the antigen. In another aspect, characterization can include quantifying the relative abundance of the antibody and/or antigen in an antigen-antibody complex.

In some exemplary embodiments, the sample can comprise at least two proteins.

In some exemplary embodiments, the antibody-drug conjugate can include site-specific ADC or non-site-specific ADC. In one aspect, the antibody-drug conjugate can include non-site-specific ADCs linked through cysteine or lysine residues on the antibody. In another aspect, the antibody-drug conjugate can include site-specific ADCs linked through natural amino acids, unnatural amino acids, glycans, short peptide tag, or combinations thereof.

In some exemplary embodiments, the electrospray ionization mass spectrometer can be a tandem mass spectrometer.

In some exemplary embodiments, the protein can be a therapeutic antibody, an antibody, a monoclonal antibody, a polyclonal antibody, a bispecific antibody, an antibody fragment, a fusion protein, or combinations thereof. In one aspect, the antibody fragment can include Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In some exemplary embodiments, the protein can be a digestion product of the antibody. The digestion product can be formed by a hydrolyzing agent. The digestion product can be a product-related impurity.

In some exemplary embodiments, the protein can be a product-related impurity present in a biopharmaceutical.

In some exemplary embodiments, the protein can have a pI in the range of about 4.5 to about 9.0. In one aspect, the protein can have a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In one exemplary embodiment, the sample can comprise at least two proteins.

It is understood that the methods are not limited to any of the aforesaid protein, impurity, and column and that the methods for identifying or quantifying may be conducted by any suitable means.

Figure 2:
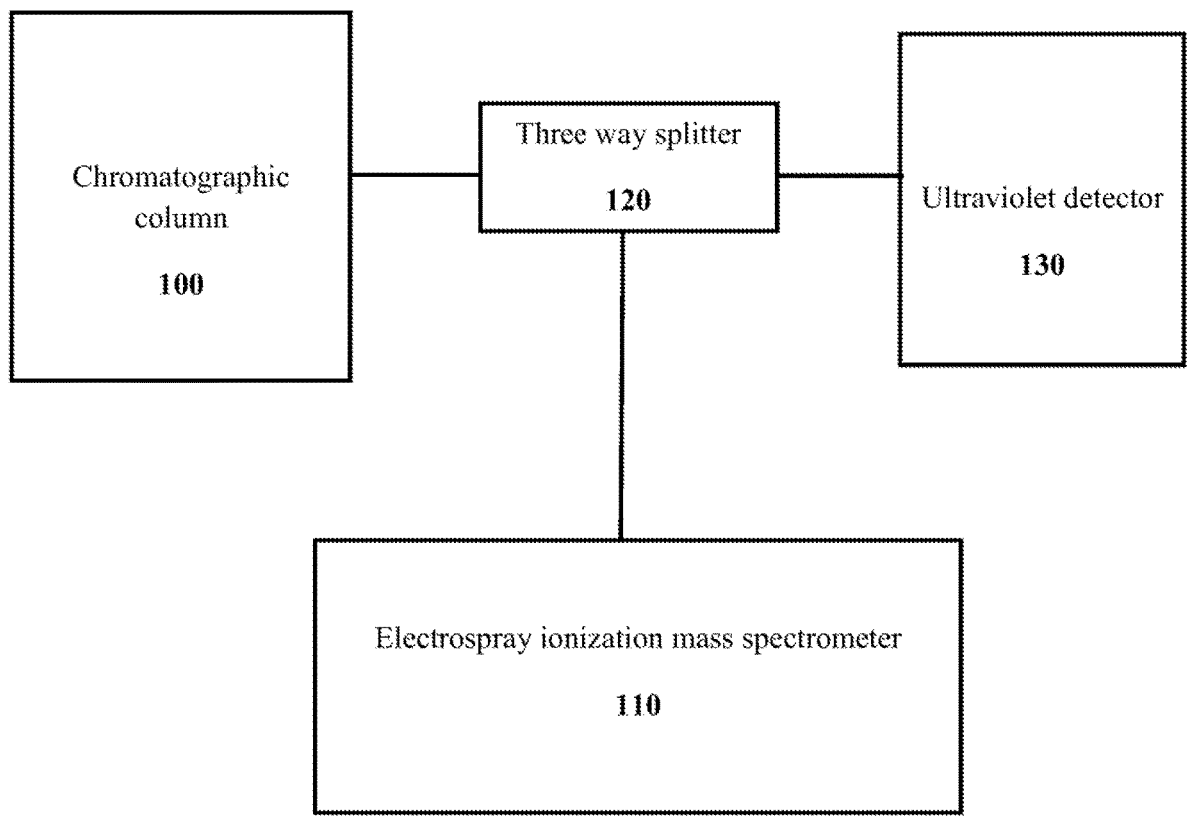
FIG. 2 shows an exemplary embodiment of a system capable of characterizing protein biopharmaceuticals.

In some exemplary embodiments, this disclosure provides a system comprising a chromatographic column 100 having a chromatography resin, wherein the chromatographic column is capable of receiving a mobile phase and a sample including a protein, and an electrospray ionization mass spectrometer 110 (See FIG. 2).

In some exemplary embodiments, the chromatographic column 100 can have a resin selected from hydrophobic interaction chromatography resin, anion exchange resin, anion exchange resin, affinity chromatography rein, size exclusion chromatography resin, a mixed mode resin, or combinations thereof.

In some exemplary embodiments, the electrospray ionization mass spectrometer 110 can be capable of being coupled to said chromatographic column 100.

In some exemplary embodiments, the electrospray ionization mass spectrometer 110 can be capable of being run under native conditions.

In some exemplary embodiments, the electrospray ionization mass spectrometer 110 can be a nano electrospray ionization mass spectrometer.

In some exemplary embodiments, the electrospray ionization mass spectrometer 110 can be a nano electrospray ionization mass spectrometer run under native conditions.

In some exemplary embodiments, the chromatographic column 100 can be capable of being coupled to the electrospray ionization mass spectrometer 100 using a three way splitter 120.

In some exemplary embodiments, the chromatographic column 100 can be capable of being coupled to an ultraviolet detector 130 using a three way splitter 120.

In some exemplary embodiments, the chromatographic column 100 can be capable of being coupled to an ultraviolet detector 130 and the electrospray ionization mass spectrometer 110 using a three way splitter 120.

In some exemplary embodiments, the three way splitter 120 can be capable of being disproportionately split to allow a flow from the chromatographic column 100 to an ultraviolet detector 130 and the electrospray ionization mass spectrometer 110.

In some exemplary embodiments, the system can be capable of characterizing drug to antibody ratio of an antibody-drug conjugate.

In some exemplary embodiments, the system can be capable of characterizing a protein.

In some exemplary embodiments, the system can be capable of characterizing an antigen-antibody complex.

Figure 3:
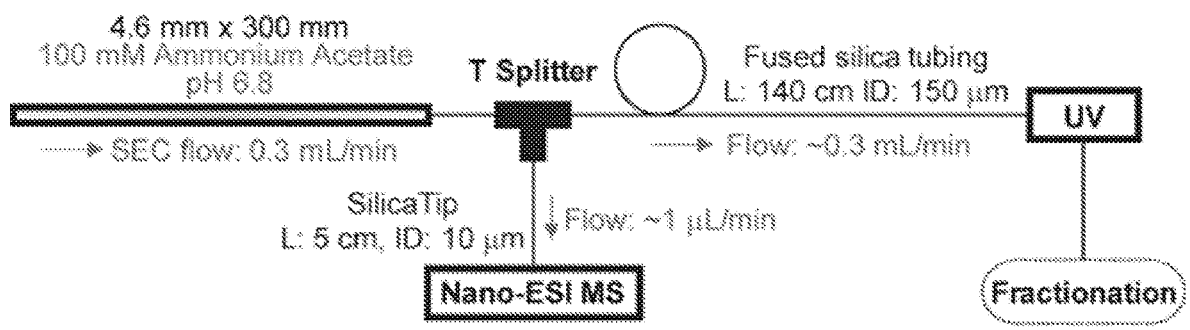
FIG. 3 shows an exemplary embodiment of a system capable of characterizing protein biopharmaceuticals.

An exemplary embodiment of the system in displayed in FIG. 3. A post-column three way-splitter is used to enable UV/MS dual detection. The low volume fraction can be directed to the MS while the high volume fraction is transferred to the UV detector. Detection almost shares the same retention times. Fractions from the UV detector can be collected for sample recovery.

Figure 4:
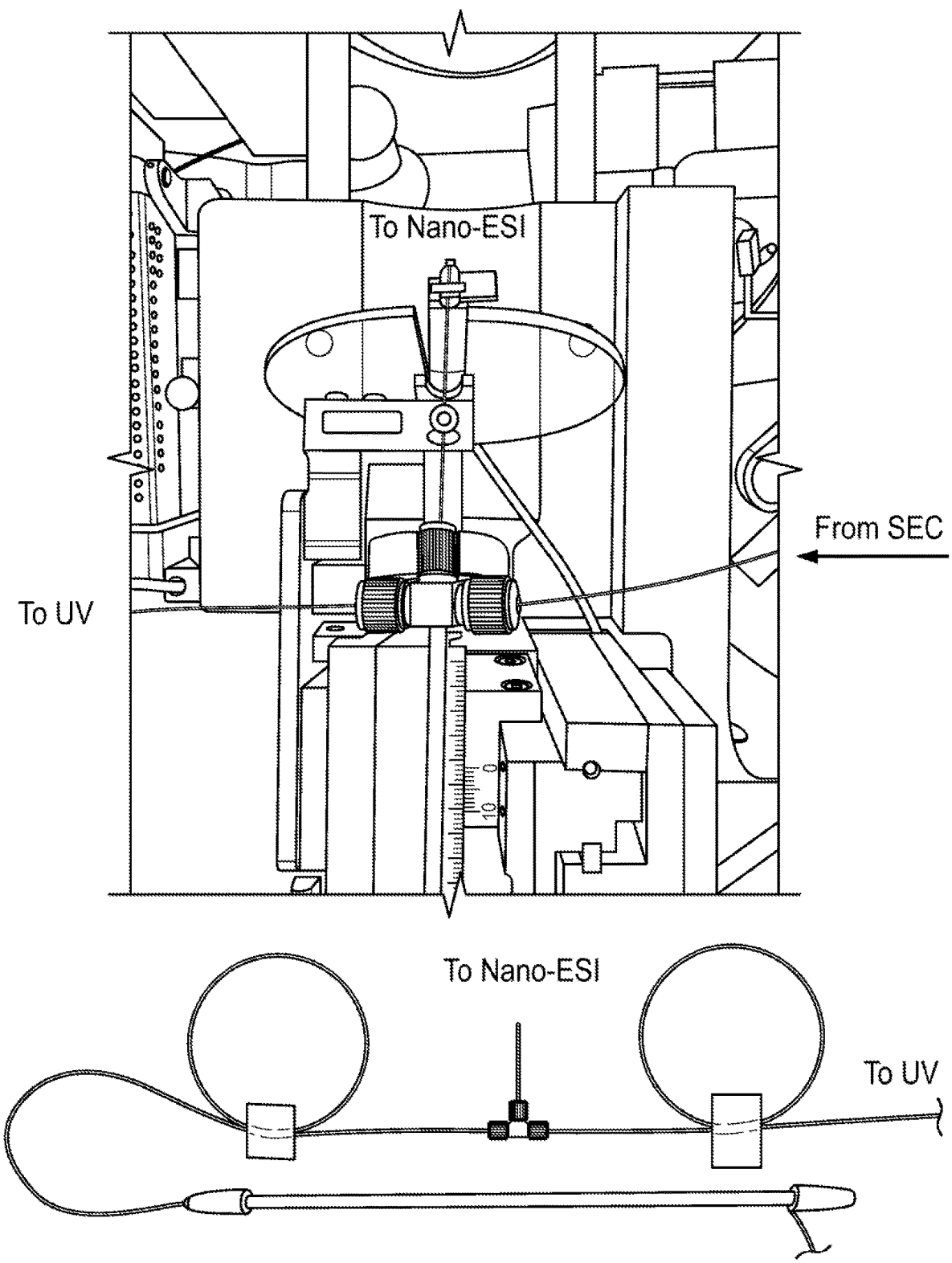
FIG. 4 shows a setup for a system capable of characterizing protein biopharmaceuticals according to one exemplary embodiment.

Another figure of the setup according to one exemplary embodiment is shown in FIG. 4.

It is understood that the system is not limited to any of the aforesaid protein, chromatography column, mass spectrometer, antibody-drug conjugate, antigen-antibody complex.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is herein incorporated by reference, in its entirety and for all purposes.

The disclosure will be more fully understood by reference to the following Examples, which are provided to describe the disclosure in greater detail. They are intended to illustrate and should not be construed as limiting the scope of the disclosure.

EXAMPLES

Materials and reagents. Water was purchased from Honeywell (Muskegon, MI). Ammonium acetate was purchased from Sigma-Aldrich (St Louis, MO). 1 M Tris-HCl, pH 7.5 was purchased from Teknova (Hollister, CA). Fused silica tubing (inner Diameter (ID) 150 µm, outer diameter (OD)

360 µm), 3-way connector and sleeve were purchased from IDEX (Oak Harbor, WA). PicoTip EMITTER SilicaTip (FS360-20-10-D-20-7CT) was purchased from New Objective (Woburn, MA). ACQUITY UPLC Protein BEH SEC Column, 200 Å, 1.7 µm, 4.6×300 mm was purchased from Waters (Milford, MA). Hot pocket column heater was purchased from Thermo-Fisher (Waltham, MA). All reagents were used without additional purification.

Online SEC-nano-ESI-MS analysis. ACQUITY UPLC I class system (Waters, Milford, MA) was coupled to Q Exactive HF hybrid quadrupole-Orbitrap mass spectrometer (Thermo Scientific, Bremen, Germany) for all online SEC-nano-ESI-MS analyses. ACQUITY UPLC Protein BEH SEC Column (200 Å, 1.7 µm, 4.6×300 mm) was set at 30° C. and used for mAbs and ADCs separation. Mobile phase was 100 mM ammonium acetate at pH 6.8. Each separation was 30 minutes with a flow rate of 0.3 mL/min, and the injection amount was set to 40 µg. A three-way splitter (T-splitter) was connected after the SEC column. Fused silica tubing (L: 140 cm, ID: 150 µm) and SilicaTip (L: 5 cm, ID: 10 µm) were connected to the T-splitter. The high volume fraction was transferred to the UV detector via fused silica tubing, while the low volume fraction was diverted to the MS via a SilicaTip. The following MS parameters were used for online SEC-nano-ESI-MS data acquisition. Each acquisition was 25 minutes beginning immediately after sample injection. Samples were ionized in positive mode with 3 kV spray voltage, 200° C. capillary temperature, and 70 S-lens RF level. In-source CID was set at 75 eV. Full MS scans were acquired at 15 K resolving power with mass range between m/z 2000-8000. A maximum injection time of 100 ms, automatic gain control target value of 3e6, and 10 microscans were used for full MS scans.

Data analysis. Protein Metrics Intact Mass software was used for raw data deconvolution. Thermo Xcalibur Qual Browser was used for extracted ion chromatogram analysis. Microsoft Excel was used for DAR calculation of ADCs.

Example 1. Investigation of Antigen-Antibody Interactions with Online SEC-Nano-ESI-MS In order to develop effective antibody therapeutics, it can be crucial to understand how antibody binding affects the function of the targeted protein.

1.1 Online SEC-Nano-ESI-MS Instrumentation

SEC and MS technologies are routinely used for characterizing protein samples. SEC allows for the isolation and characterization of proteins under conditions that minimize changes in protein structure, while MS permits the identification of individual components in complex samples. Combining the individual capabilities of SEC and MS into a single platform would be highly desirable, but has proven challenging because the high flow rate and nonvolatile salts used for SEC analyses are incompatible with native MS. To overcome this limitation, reduction of solvent and salt intake into the MS by splitting the flow of eluate from the SEC using a post-column T-splitter was performed (See FIG. 3). A picture of the set-up is shown in FIG. 4. The T-splitter was then connected to the MS via a SilicaTip and, in parallel, to a UV detector via fused silica tubing. This arrangement enabled simultaneous, dual UV/MS detection of SEC elutes. By varying the length and diameter of the fused silica tubing, flow rate to the MS via the SilicaTip could be regulated (e.g. longer/narrower tubing can generate higher resistance causing increased flow to the SilicaTip and MS). Protein samples were separated with a 4.6 mm SEC column using a 0.3 mL/min flow rate. The fused silica tubing connecting T-splitter and UV detector with a length of 140 cm and an inner diameter of 150 µm resulted in a desirable flow rate of ~1 µL/min to the SilicaTip. The length and diameter of the fused silica tubing also enabled near synchronous detection of molecules by the UV and MS.

1.2 Antigen-Antibody Complex

The complex formed between a previously reported antibody (Qian Zhang et al., *Epitope Mapping by HDX-MS Elucidates the Surface Coverage of Antigens Associated with High Blocking Efficiency of Antibodies to Birch Pollen Allergen*, 90 ANALYTICAL CHEMISTRY 11315-11323 (2018)) against recombinant Bet v 1 and the Bet v 1 antigen under native MS conditions.

Figure 5A:
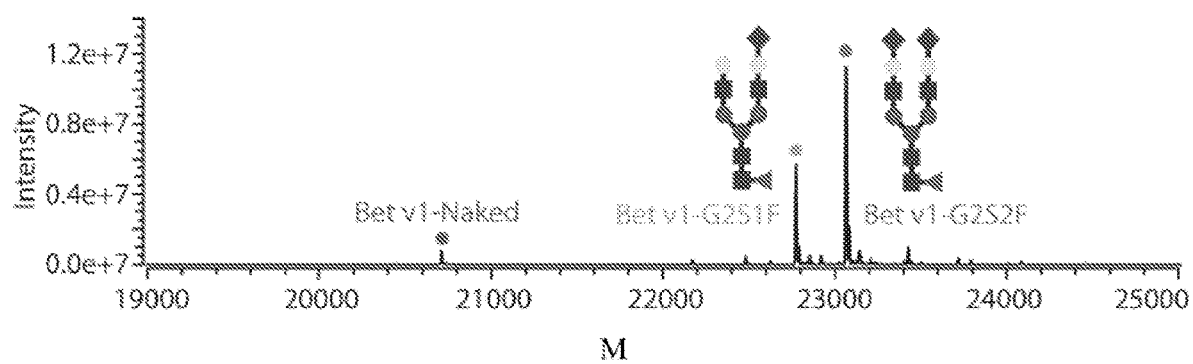
FIGS. 5A and 5B show analysis of antigen-antibody complex with system capable of characterizing protein biopharmaceuticals according to one exemplary embodiment.
Figure 5B:
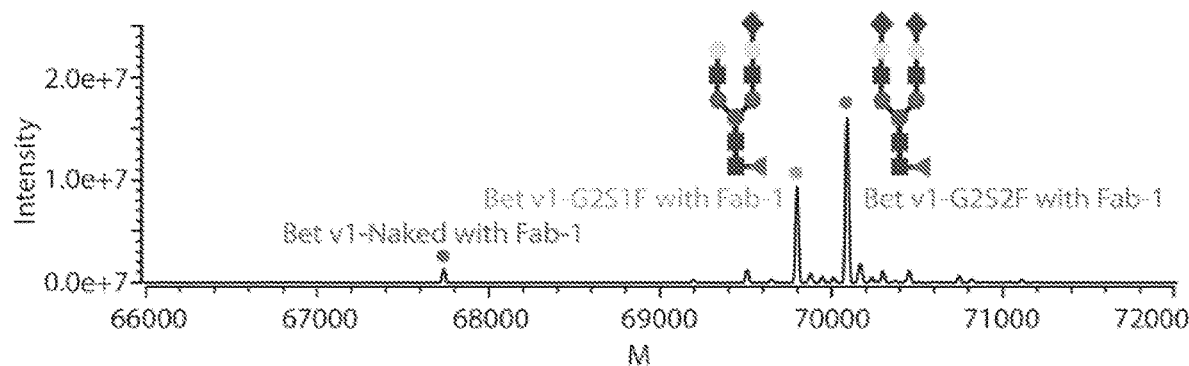

Other than the naked form, two major glycosylated forms were observed for Bet v 1 including G2S1F and G2S2F as seen in FIG. 5. After incubation with equal molar amounts of a Fab-1 antibody, all three Bet v 1 forms (naked, G2S1F and G2S2F) bound Fab-1 as a one antigen to one Fab complex. In FIG. 5A, the deconvoluted native MS spectrum of the Bet v 1 antigen alone revealed three different Bet v 1 species: naked Bet v 1 and two major glycosylated forms, Bet v 1 G2S1F and G2S2F. Incubation of Bet v 1 antigen with equal molar amounts of the Bet v 1 Fab-1 antibody demonstrated that all three Bet v 1 forms (naked, G2S1F and G2S2F) complex with Fab-1 in a one antigen to one Fab ratio (FIG. 5B). It appears that glycosylation does not affect the formation of the antibody/antigen complex because the relative abundance of the MS signal for all Bet v 1 forms was similar between unbound and Fab-1 bound conditions.

Figure 6:
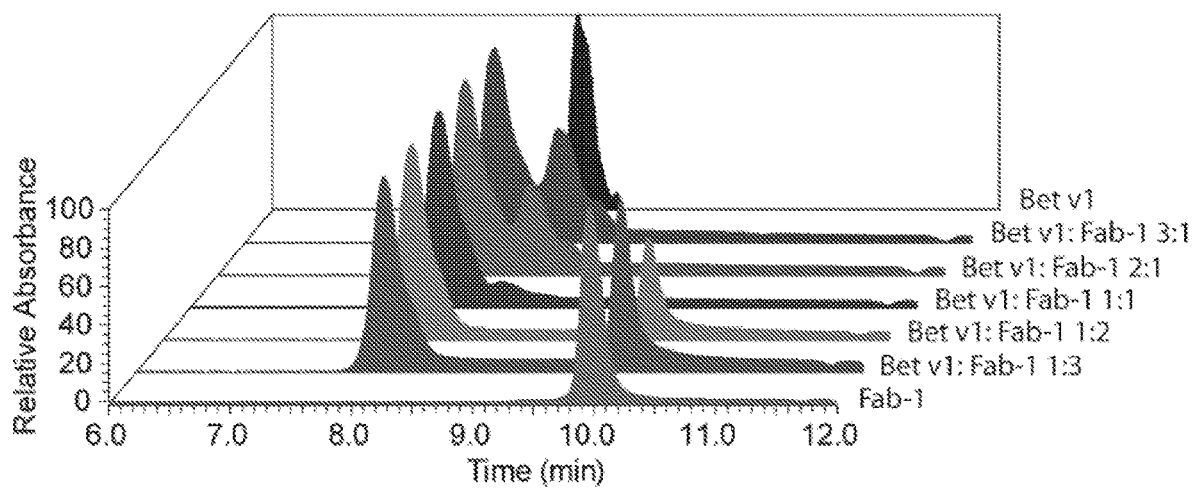
FIG. 6 shows the results of antigen-antibody titration between Bet v 1 and Fab-1 characterized according to an exemplary embodiment.

To further characterize the antigen-antibody interaction, a titration experiment was performed on the MS and UV dual detection platform. Several different ratios of Bet v 1 to Fab-1 were examined by UV as shown in FIG. 6. Bet v 1 alone (black) eluted at 8.5 min, while Fab-1 alone (teal) and the Bet v 1:Fab-1 complex eluted at 9.8 min and 7.9 min, respectively. The stoichiometry of the Bet v 1:Fab-1 complex revealed a 1:1 binding ratio. No additional stoichiometries were observed with excess amounts of either the antigen or antibody. Further, mixing Bet v 1 antigen with Fab-1 in an exact 1 to 1 molar ratio minimized the amount free antigen and antibody (blue).

Figure 7A:
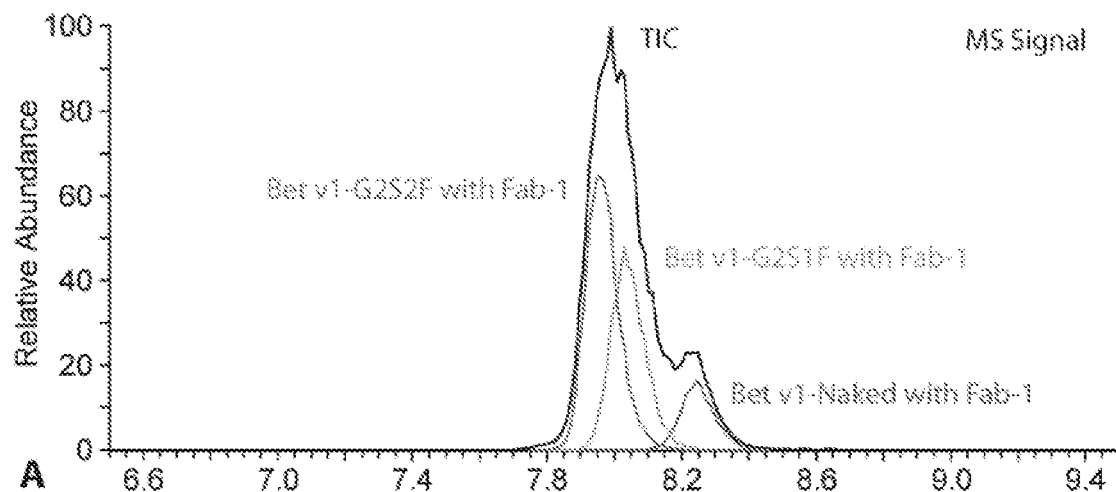
FIG. 7A shows the mass spectrometer signal as a result of dual detection by ultraviolet detector and native electrospray ionization mass spectrometer antigen-antibody interaction between Bet v 1 and Fab-1 for under native conditions according to an exemplary embodiment
Figure 7B:
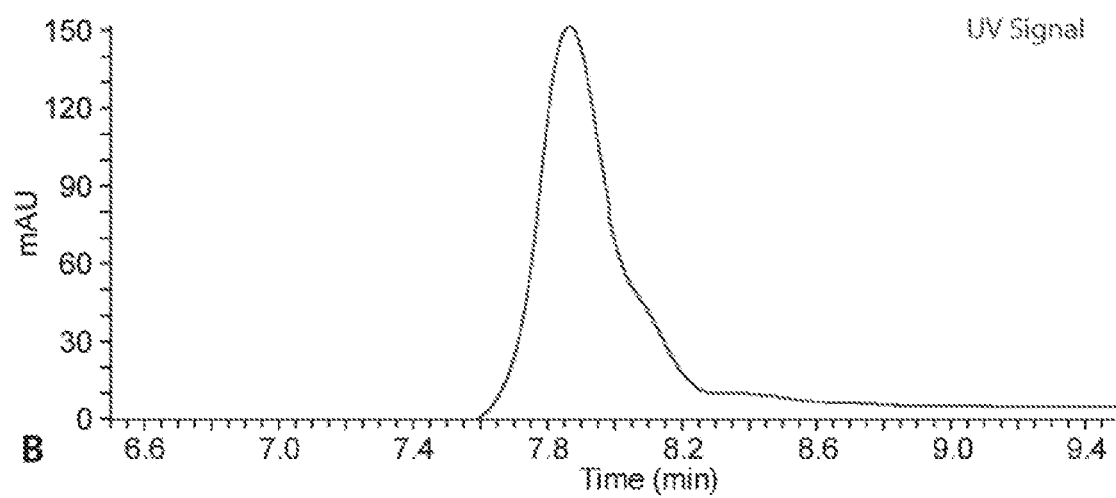
FIG. 7B shows the ultraviolet signal result as a result of dual detection by ultraviolet detector and native electrospray ionization mass spectrometer antigen-antibody interaction between Bet v 1 and Fab-1 for under native conditions according to an exemplary embodiment.

While UV peaks can represent the relative abundance for individual proteins in solution, MS allows for the identification of individual components in complex samples. With the dual detection of UV and MS, one can determine all species co-eluting within the same UV peak or in across different UV peaks. As shown in FIG. 7, MS analysis of the UV peak that eluted at 7.9 minutes revealed three different complexes formed by the Fab-1 bound to each of the three different Bet v 1 species (naked, G2S1F and G2S2F). We found that the Fab-1: naked complex eluted after the Fab-1 in complex with the glycosylated Bet v 1 species, which may be attributed to the larger hydrodynamic radius provided by the glycans. Minimizing the delay in detection between the UV and MS enabled the collection of fractions from the UV detector for sample recovery. This method is particularly useful for determining whether cleaved, modified, or mutated versions of an antigen and/or antibody retains binding without having to purify specific forms of the proteins understudy.

Example 2. Characterization of Cysteine ADCs with Online SEC-Nano-ESI-MS

Antibody drug conjugates (ADC) are highly potent therapeutics that can specifically deliver small molecule drugs to target tissue by their conjugation to antibodies (François Debaene et al., *Innovative Native MS Methodologies for Antibody Drug Conjugate Characterization: High Resolution Native MS and IM-MS for Average DAR and DAR Distribution Assessment*, 86 ANALYTICAL CHEMISTRY 10674-10683 (2014)). The potency, efficacy and toxicity of ADCs can highly depend on the number of small molecule drugs conjugated to each antibody. Therefore, it can be critical to determine the drug to antibody ratio (DAR) for each ADC. Conjugation through interchain cysteines is one of the most common approaches for conjugating small molecule drugs to antibodies. For interchain cysteine-based ADCs, unpaired interchain cysteine residues can be introduced by engineering primary sequence mutations (site-specific interchain cysteine-based conjugates) or through partial reduction of the antibody (random interchain cysteine-based conjugates). Site-specific conjugation of engineered mAbs provides for better control over the DAR of the ADC, whereas conjugations performed on partially reduced mAbs will yield a more variable range of DAR (zero to eight). However, it can still be necessary to determine the DAR of ADCs generated by either method to understand and interpret the biological effects of these drug conjugates. The most common method for determining DAR of cysteine based ADCs is via HIC-UV (Laura R. Saunders et al., *A DLL3-targeted antibody-drug conjugate eradicate's high-grade pulmonary neuroendocrine tumor-initiating cells in vivo*, 7 SCIENCE TRANSLATIONAL MEDICINE (2015) or RPLC-MS under reduced/denatured conditions. Recently, however, Debaene et al. reported an offline desalting SEC method coupled with high resolution native MS and IM-MS for average DAR measurement. Native MS analysis is the only way to analyze the DAR for cysteine conjugated ADCs without disrupting the intact molecule.

1.1 Online SEC-Nano-ESI-MS Instrumentation

The instrumentation as illustrated in 1.1 was used.

1.2 Cysteine Based Site-Specific Conjugated ADC

Figure 8A:
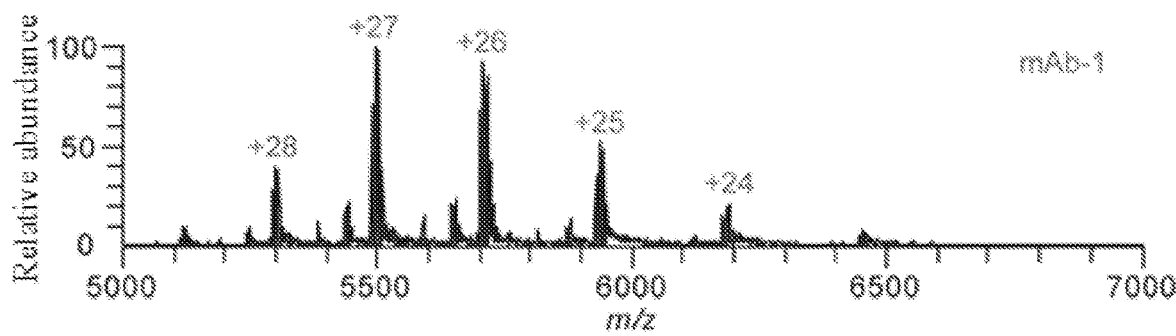
FIG. 8A shows a raw spectrum of parent mAb-1 drug-to-antibody ratio analysis of site-specific conjugated cysteine ADC-1 by online SEC-nano-ESI-MS instrumentation according to an exemplary embodiment.
Figure 8B:
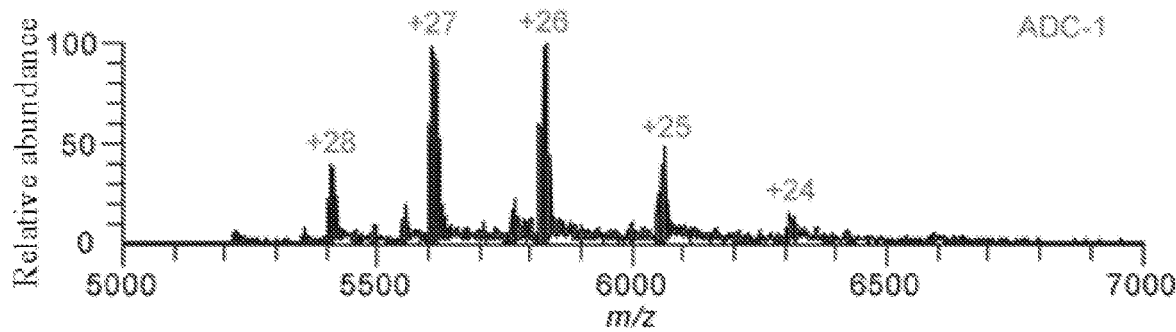
FIG. 8B shows a raw spectrum of ADC-1 drug-to-antibody ratio analysis of site-specific conjugated cysteine ADC-1 by online SEC-nano-ESI-MS instrumentation according to an exemplary embodiment.
Figure 8C:
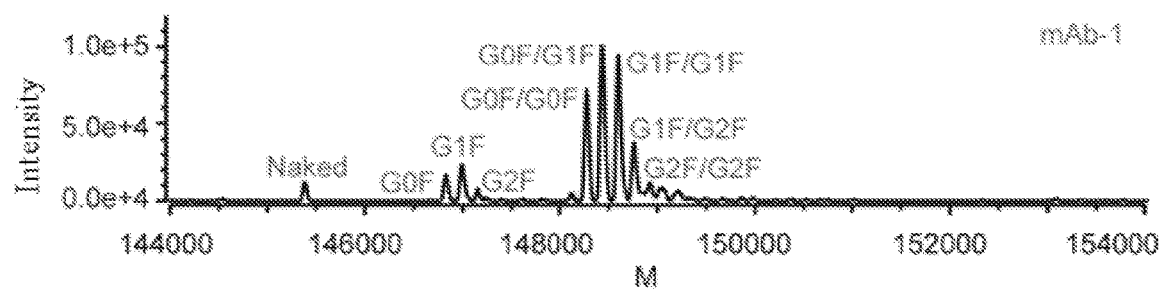
FIG. 8C shows a convoluted spectrum of parent mAb-1 drug-to-antibody ratio analysis of site-specific conjugated cysteine ADC-1 by online SEC-nano-ESI-MS instrumentation according to an exemplary embodiment.
Figure 8D:
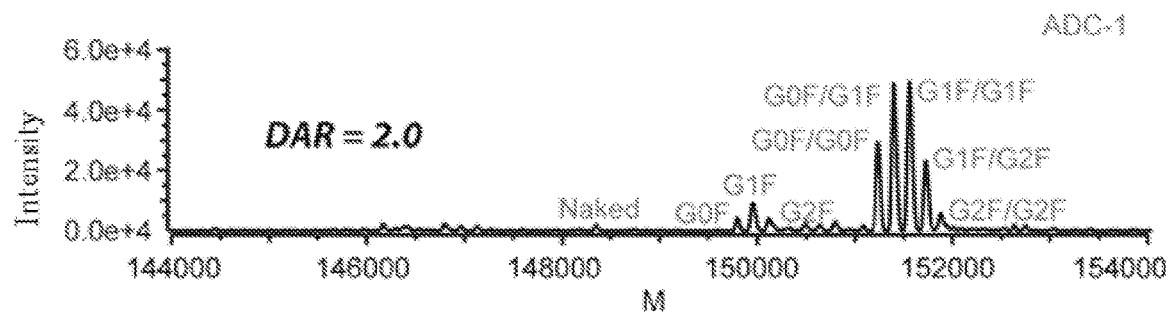
FIG. 8D shows a convoluted spectrum of ADC-1 drug-to-antibody ratio analysis of site-specific conjugated cysteine ADC-1 by online SEC-nano-ESI-MS instrumentation according to an exemplary embodiment.
Figure 9:
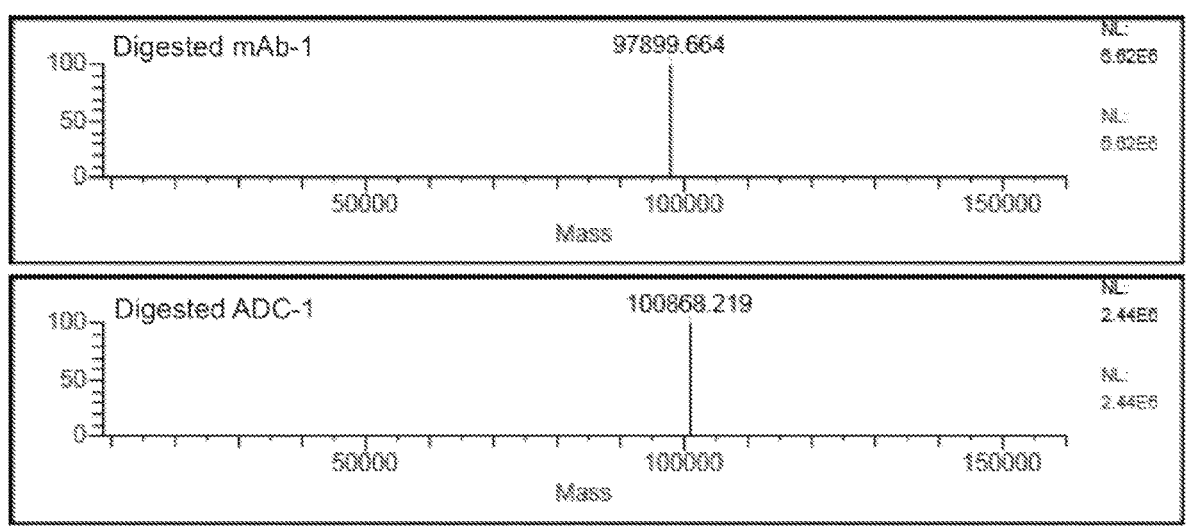
FIG. 9 shows a drug-to-antibody ratio analysis of site-specific conjugated cysteine mAb-1 and ADC-1 by FabRICATOR digestion and online SEC-nano-ESI-MS instrumentation according to an exemplary embodiment.

The DAR of cysteine based site-specific conjugated ADCs using online SEC-nano-ESI-MS system was evaluated. Mutations to interchain cysteines on the mAb heavy chains introduced two unpaired cysteines on the light chains of the mAb, which were conjugated to drug to yield DAR 2 antibody species. As shown in FIG. 8, raw and deconvoluted spectra of the parent mAb-1 and ADC-1 indicate that only a DAR 2 form is present in the ADC sample. Deconvoluted spectra in FIG. 8A-C show various glycans are present on both the parental mAb-1 and conjugated ADC-1. Along with the non-glycosylated mAb-1, partially and fully glycosylated mAb-1 species, having various combinations of G0F, G1F and G2F, were all conjugated with 2 drugs. These results were confirmed by analyzing fabricator digested mAb-1 and ADC-1 as shown in FIG. 9. A few ADCs with similar conjugation chemistry has been tested and showed DAR 2 form only (data not shown).

1.3 Non-Site-Specific Cysteine Conjugated ADC

Figure 10A:
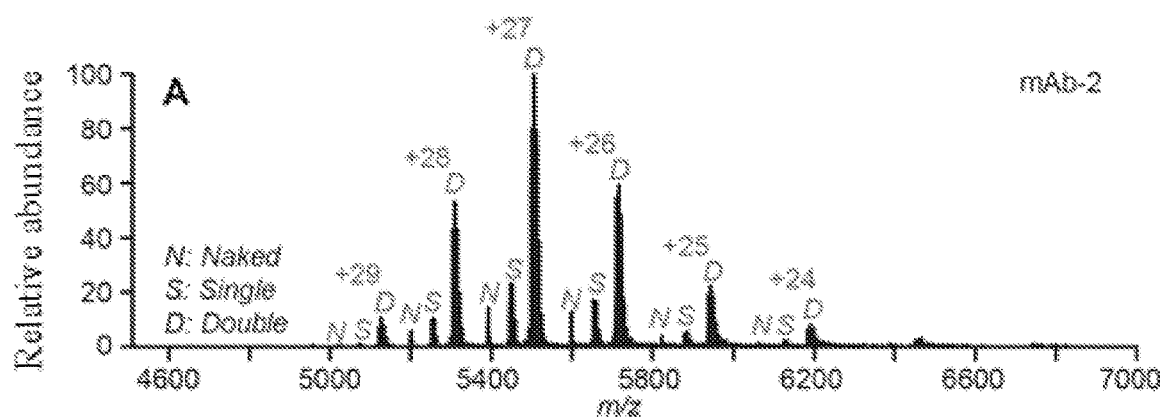
FIG. 10A shows a raw spectra of parent mAb-2 drug-to-antibody ratio analysis of site-specific conjugated cysteine ADC-2 by online SEC-nano-ESI-MS instrumentation according to an exemplary embodiment, wherein N means that the antibody has no glycan, S means that the glycosylation is with a single chain of the antibody and D means the glycosylation is with both chains of the antibody.
Figure 10B:
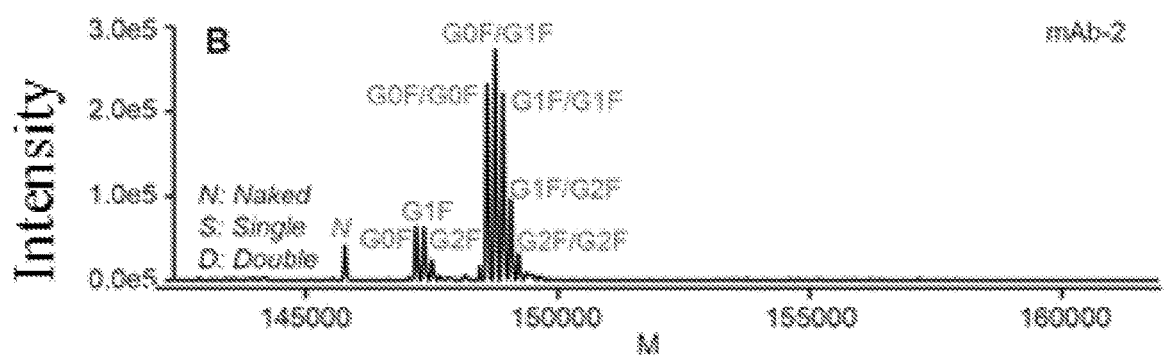
FIG. 10B shows a convoluted spectra of parent mAb-2 drug-to-antibody ratio analysis of site-specific conjugated cysteine ADC-2 by online SEC-nano-ESI-MS instrumentation according to an exemplary embodiment, wherein N means that the antibody has no glycan, S means that the glycosylation is with a single chain of the antibody and D means the glycosylation is with both chains of the antibody.
Figure 10C:
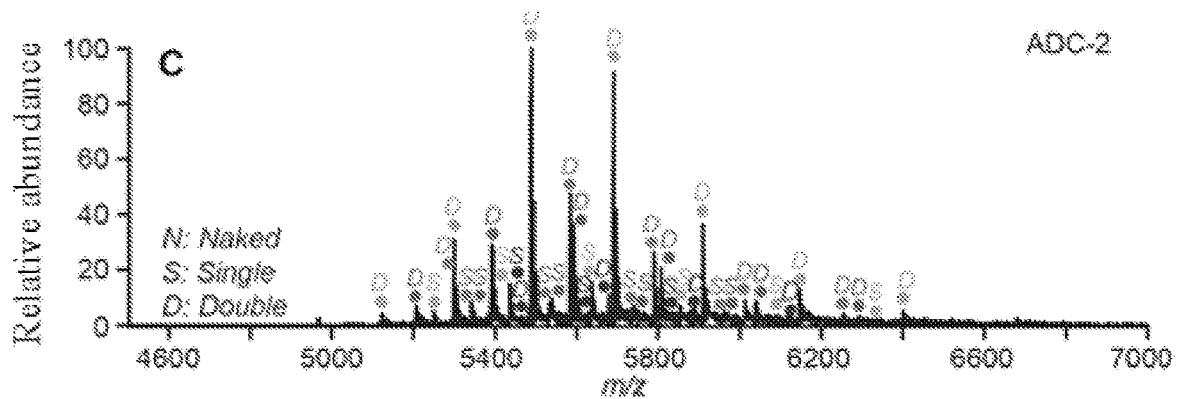
FIG. 10C shows a raw spectra of ADC-2 drug-to-antibody ratio analysis of site-specific conjugated cysteine ADC-2 by online SEC-nano-ESI-MS instrumentation according to an exemplary embodiment, wherein N means that the antibody has no glycan, S means that the glycosylation is with a single chain of the antibody and D means the glycosylation is with both chains of the antibody.
Figure 10D:
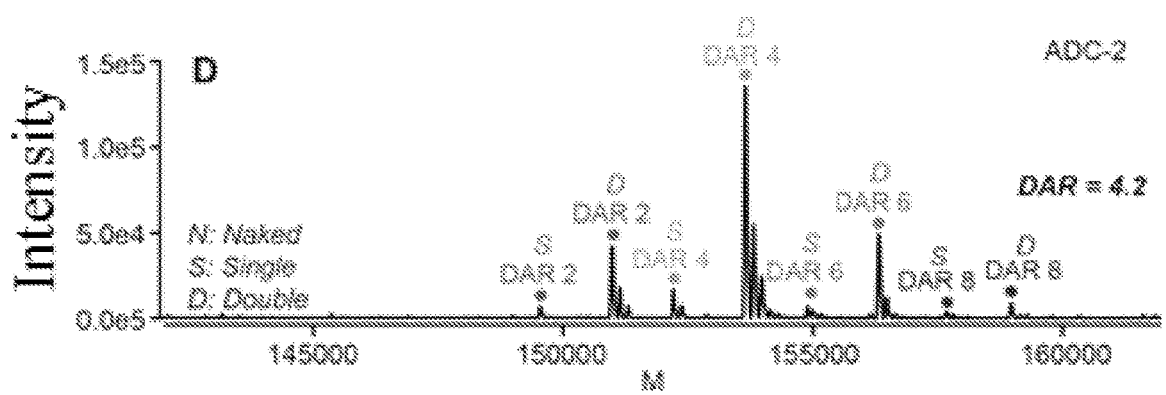
FIG. 10D shows a convoluted spectrum of parent ADC-2 drug-to-antibody ratio analysis of site-specific conjugated cysteine ADC-2 by online SEC-nano-ESI-MS instrumentation according to an exemplary embodiment, wherein N means that the antibody has no glycan, S means that the glycosylation is with a single chain of the antibody and D means the glycosylation is with both chains of the antibody.

In addition to analyzing site-specific ADC, the DAR of drug conjugated to interchain cysteines of partially reduced mAbs was also investigated. The raw and deconvoluted spectra of non-site-specific cysteine conjugated ADC generated using similar chemistry are shown in FIG. 10. ADC-2 was generated with an unmodified parental antibody with normal glycosylation. Raw and deconvoluted spectra of parent mAb-2 (FIG. 10A-B) and ADC-2 (FIG. 10C-D) show DAR values that vary from 2-8 for ADC-2. Deconvoluted spectra also show various glycans present on mAb-2 (FIG. 10B) and ADC-2 (FIG. 10D).

An online SEC-nano-electrospray ionization (nano-ESI)-MS platform with dual ultraviolet (UV) and MS detection was developed. The utility of this platform was validated by examining non-covalent protein interactions by using it for characterizing the antigen-antibody complexes that result from titration experiments and determining the drug-to-antibody ratio (DAR) of cysteine-based antibody-drug conjugates (ADCs). This platform can be easily modified and, therefore, can be adapted for analyzing other native MS projects such as the characterization of monoclonal antibody (mAb) charge variants or large, aggregated protein complexes.

The three way splitter was used to disproportionately split SEC eluates to a MS and UV detector, with the low-volume fraction directed to the MS and the high-volume fraction directed to the UV detector. The current platform enabled complementary dual detection by UV and native-MS, with the possibility of fraction collection, and can be applied to the characterization of antigen-antibody complexes and DAR analysis of interchain cysteine conjugated ADCs. Further modifications to this online SEC-nano-ESI-MS platform, such as changing the column chemistry or using a Q Exactive UHMR instrument, would allow it to be adapted for other applications such as analyzing charge variants or very large protein complexes. The method described herein unlocked the possibility of combining high salt separation techniques (i.e. HIC, WCX) with mass spectrometry-based detection. In conclusion, the online SEC-nano-ESI-MS platform could be broadly applied to the analysis of protein biopharmaceuticals for a variety of applications.

What is claimed is:

1. A method for determining a drug to antibody ratio for an antibody-drug conjugate, said method comprising:
   contacting a sample including the antibody-drug conjugate to a chromatographic system having a size-exclusion chromatography resin;
   washing said size-exclusion chromatography resin using a mobile phase to provide an eluent including the antibody-drug conjugate; and
   determining the drug to antibody ratio from spectra obtained using an electrospray ionization mass spectrometer under native conditions.

2. The method of claim 1, wherein the antibody-drug conjugate has a cysteine based site-specific conjugation.

3. The method of claim 1, wherein the antibody-drug conjugate has a cysteine based non-site-specific conjugation.

4. The method of claim 1, wherein the antibody-drug conjugate has a lysine based conjugation.

5. The method of claim 1, wherein the electrospray ionization mass spectrometer is coupled to the chromatographic system having the size-exclusion chromatography resin.

6. The method of claim 1, wherein the electrospray ionization mass spectrometer is a nano-electrospray ionization mass spectrometer.

7. The method of claim 1, wherein at least one three way-splitter is used to couple the electrospray ionization mass spectrometer to the chromatographic system having the size-exclusion chromatography resin.

8. The method of claim 1, wherein at least one three way-splitter is used to couple an ultraviolet detector to the chromatographic system having the size-exclusion chromatography resin.

9. The method of claim 8, wherein the eluent from washing the size-exclusion chromatography resin is introduced to the ultraviolet detector through the at least one three way-splitter at a flow rate of about 0.2 mL/min to about 0.4 mL/min.

10. The method of claim 1, wherein the mobile phase used to wash the size-exclusion chromatography resin comprises ammonium acetate.

11. The method of claim 1, wherein the mobile phase used to wash the size-exclusion chromatography resin comprises a volatile salt.

12. The method of claim 1, wherein the mobile phase used to wash the size-exclusion chromatography resin has a total concentration of about 100 mM.

13. The method of claim 1, wherein the mobile phase used to wash the size-exclusion chromatography resin has a flow rate of about 0.2 mL/min to about 0.4 mL/min.

14. The method of claim 1, wherein the mobile phase used to wash the size-exclusion chromatography resin has a pH of about 6.8.

15. The method of claim 1, wherein an amount of the sample including the antibody-drug conjugate contacted to the chromatography system is about 10 μg to about 100 μg.

16. The method of claim 1, wherein the eluent provided from washing the size-exclusion chromatography resin is introduced to the electrospray ionization mass spectrometer at a flow rate of less than about 50 μl/min.

17. The method of claim 1, wherein the eluent provided from washing the size-exclusion chromatography resin is introduced to the electrospray ionization mass spectrometer, wherein a flow rate of electrospray from the electrospray ionization is about 10 nL/min to about 50 nL/min.

18. The method of claim 1, wherein the antibody-drug conjugate is an engineered cysteine-based antibody-drug conjugate.

19. The method of claim 1, wherein the antibody-drug conjugate is a non-specific cysteine-based antibody-drug conjugate.

20. The method of claim 1, wherein characterizing the antibody-drug conjugate comprises characterizing drug to antibody ratio.

* * * * *